US007358062B2

(12) United States Patent
Suovaniemi et al.

(10) Patent No.: US 7,358,062 B2
(45) Date of Patent: Apr. 15, 2008

(54) METHOD FOR DIAGNOSING ATROPHIC GASTRITIS

(75) Inventors: Osmo Suovaniemi, Helsinki (FI); Matti Härkönen, Espoo (FI); Tapani Tiusanen, Vantaa (FI); Pentti Sipponen, Espoo (FI)

(73) Assignee: Biohit Oyj, Helsinki (FI)

( * ) Notice: Subject to any disclaimer, the term of this patent is extended or adjusted under 35 U.S.C. 154(b) by 21 days.

(21) Appl. No.: 10/451,742

(22) PCT Filed: Jan. 4, 2002

(86) PCT No.: PCT/FI02/00008

§ 371 (c)(1),
(2), (4) Date: Jun. 25, 2003

(87) PCT Pub. No.: WO02/054084

PCT Pub. Date: Jul. 11, 2002

(65) Prior Publication Data

US 2004/0038376 A1 Feb. 26, 2004

(30) Foreign Application Priority Data

Jan. 5, 2001 (FI) .................................. 20010019

(51) Int. Cl.
G01N 33/573 (2006.01)
G01N 33/554 (2006.01)
(52) U.S. Cl. .................. 435/7.4; 435/7.32; 435/12; 424/234.1

(58) Field of Classification Search ................ 435/7.4, 435/7.1, 7.32, 7.23, 7.91, 7.72, 7.7, 252.3, 435/10, 12, 127, 4; 530/300
See application file for complete search history.

(56) References Cited

U.S. PATENT DOCUMENTS 4,656,025 A * 4/1987 Deutsch ................ 435/7.5

(Continued)

FOREIGN PATENT DOCUMENTS

EP 0 760 482 A2 3/1997

(Continued)

OTHER PUBLICATIONS

Hallissey, MT et al, Scand. J. Gastroenterology, vol. 29, pp. 1129-1134, 1994, Evaluation of Pepsinogen A and Gastrin-17 as markers of gastric cancer and high risk pathological conditions.*

(Continued)

*Primary Examiner*—Mark Navarro
*Assistant Examiner*—Ginny Allen Portner
(74) *Attorney, Agent, or Firm*—Birch, Stewart, Kolasch & Birch, LLP (57) ABSTRACT

The press device for a paper web, such as a calender, contains a flexible moving element (1a) forming an endless structure, said element forming the shell (1) of a roll, the press device including further a counter roll. Inside the moving element (1a) there is a shoe element (3) that is arranged to support the shell (1a) against the counter roll to form a nip (N). The width and/or the surface contour of the supporting surface of the shoe element (3) guiding the shell of the roll in the nip contact varies in the machine direction and the shoe element is positionable in the machine direction to adjust the nip width and/or length.

26 Claims, 1 Drawing Sheet

U.S. PATENT DOCUMENTS

| | | | |
|---|---|---|---|
| 6,013,463 A * | 1/2000 | Cover et al. | 435/7.92 |
| 6,156,525 A * | 12/2000 | Furuta | 435/7.4 |
| 6,696,262 B2 * | 2/2004 | Harkonen | 435/7.32 |
| 6,852,487 B1 * | 2/2005 | Barany et al. | 435/6 |
| 6,872,543 B1 * | 3/2005 | Sipponen et al. | 435/7.32 |
| 7,179,609 B1 * | 2/2007 | Mardh et al. | 435/7.2 |

FOREIGN PATENT DOCUMENTS

| | | | |
|---|---|---|---|
| EP | 0760482 A2 * | 3/1997 | |
| WO | 96/15456 * | 5/1996 | |
| WO | WO 96/15456 A1 | 5/1996 | |
| WO | 00/67029 * | 11/2000 | |
| WO | 00/67035 * | 11/2000 | |
| WO | WO 00/67035 A1 | 11/2000 | |

OTHER PUBLICATIONS

Kim, JW et al, Yonsei Medical Journal, vol. 39(2), pp. 159-165, 1998, Serum gastrin, and Pepsinogen I, II concentrations in Children with *Helicobacter pylori* infection:the Role of CagA and VacA.*

Samloff, IM et al, Relationships among serum Pepsinogen I, Serum Pepsinogen II and gastric mucosal Histology, vol. 83, Gastroenterology, pp. 204-209, 1982.*

Schlemper, RJ et al, Gut, 1995, vol. 37, pp. 199-204, Seroepidermiology of gastritis in Japanese and Dutch working populations: evidence for the development of atrophic gastritis that is not related to *Helicobacter pylori*.*

Valle, Julio et al, European Journal of Gastroenterology and Hepatology, vol. 4, pp. 985-980, 1992, Fasting serum gastrin level and peak acid output in chronic gastritis: a study on subjects in four population-based samples of Finnish people.*

Meuwissen,SGM et al, Scandinavian Journal of Gastroenterology, vol. 27(S194) 1992, pp. 1-7, Hypertrophic protein losing gastropathy-a retrospective analysis of 40 cases in the Netherlands.*

Pilotto, A et al, JAGS, vol. 44, pp. 665-670, 1996, The clinical usefulness of serum pepsinogens, Specific IgG anti-HP antibodies and gastrin for monitoring *Helicobacter pylori* treatment in Older people.*

Bonilla-Palacios, JJ et al, Serum Gastrin, Pepsinogen I, II and antibodies to *Helicobacter pylori* in patients with gastric polyps, Gastroenterology, 1993, vol. 104(4) April, p. A43 (abstract only).*

Ley et al., Cancer Epidemiology, Biomarkers & Prevention, vol. 10, pp. 107-112.

Lin et al., Journal of Gastroenterology, vol. 30, pp. 156-161 (1995).

Kuipers et al., European Journal of Gastroenterology & Hepatology, vol. 8, No. 2, pp. 153-156 (1996).

Wagner et al., The American Journal of Gastroenterology, vol. 89, No. 8, pp. 1211-1218 (1994).

J. Calam, European Journal of Clinical Investigation (1994) 24, 501-510.

PenttiP. Sipponen, In. J. Cancer: 35 173-177 (1985).

* cited by examiner

Fig.1

METHOD FOR DIAGNOSING ATROPHIC GASTRITIS

This application is the national phase under 35 U.S.C. § 371 of PCT International Application No. PCT/FI02/00008 which has an International filing date of Jan. 4, 2002, which designated the United States of America.

FIELD OF THE INVENTION

The present invention is directed to a method for assessing the state or condition of the gastric mucosa, especially for diagnosing high-risk changes in the gastric mucosa, especially atrophic gastritis, in a subject. In the method the concentration of specific analytes, namely the pepsinogen I concentration, the gastrin (preferably gastrin-17) concentration as well as the concentration or presence of a *Helicobacter pylori* marker, and optionally also the pepsinogen II concentration, is determined in the subject, and data processing means are used to process the data obtained and to provide information, for example, in the form of a diagnosis, or suggestions for further treatment or investigations.

BACKGROUND OF INVENTION

Although the occurrence of new cases of gastric cancer has diminished in the recent years, gastric cancer is still one of the most common malignancies. In Finland, appr. 250 to 300 new cases of cancer/one million people/year are registered. In the age group of people above 50, there are an estimated 2350 cases of stomach cancer, which is about 3 per mille of the age group population (Finnish Cancer Registry—The Institute for Statistical and Epidemiological Cancer Research 1993). In addition to Finland, there is a high gastric cancer incidence in Iceland, South America and especially in Japan and China.

The prognosis of gastric cancer is usually poor, as there is no specific treatment. Presently the only possibility of successfully treating gastric cancer is its early detection and total removal surgically.

Gastric cancer does not necessarily give any symptoms in its early stages. The late appearance of symptoms naturally delays the patient from seeking treatment. On the other hand, the clinical findings in the early stage of gastric cancer are often non-specific. The primary diagnostic method for gastric cancer is presently gastroscopy and biopsies, cell and aspiration cytology associated therewith. As routine gastroscopies are carried out in order to examine symptoms, such as pain in the upper abdomen or bleeding of the gastrointestinal tact, a symptomatic gastric cancer discovered in this manner is often already far advanced and thus inoperable. Attempts have also been made at improving primary diagnostics with various immunological methods, but no sufficiently specific immunological method has been successfully developed.

It is a primary object to find the means by which it would be possible to identify within the general population easily and with moderate costs those persons which might be suffering from gastric cancer in its initial stages. After identification these persons should immediately be examined by gastroscopy. At the same time those persons could be identified which exhibit premalignant gastric changes which need to be followed up.

Gastric cancer can be preceded by a number of different gastric diseases or conditions (so called precancerous conditions), which are chronic atrophic gastritis, pernicious anaemia, ventricular ulcer, gastric polyposis and the Ménétrier disease (giant hypertrophic gastritis). Clearly identifiable changes of the mucosa are dysplasia and adenoma. The said conditions are associated with an appr. 4 to 5 fold relative cancer risk, as compared to the general population. It has been established that in almost all diseases the risk is mediated over chronic atrophic gastritis.

Chronic gastritis means a prolonged inflammatory condition of the gastric mucosa. The disease can coarsely be divided into the so-called superficial and the atrophic form. In superficial gastritis, the inflammatory cell infiltration is concentrated below the surface epithelium. In case the inflammation progresses and diffuses between the specific gastric secretory glands, one refers to chronic atrophic gastritis. In such a case, the normal glandular structures of the gastric mucosa are at least partly substituted by metaplastic changes.

The relative risk of gastric cancer in patients suffering from atrophic gastritis in the corpus area of the stomach, has been estimated, as calculated from the Finnish cancer statistics, to be about 4- to 5-fold as compared to persons having a healthy mucosa. In addition, there is a risk for falling ill with pernicious anaemia due to intrinsic factor deficiency and B12 vitamin absorption disturbance. In severe atrophy of the antrum area, the risk is even 18-fold. If atrophic changes appear both in the antrum and the corpus area (pangastritis), the risk can increase to even 90-fold (Sipponen, P, Kekki, M, Haapakoski, J. Ihamäki, T & Siurala, M (1985) Gastric cancer risk in chronic atrophic gastritis: statistical calculations of cross-sectional data Int J Cancer 35:173-77).

*Helicobacter pylori* is a spiral shaped, gram-negative bacterium which thrives in the mucus in the immediate vicinity of the surface epithelial cells of the gastric mucosa and in the cell interstices. The bacterium apparently is transmitted perorally from one person to the other. The effect of the bacterium on the gastric mucosa is an inflammation reaction, which is mediated over a complement by liberating strong inflammation mediator substances. After the acute stage, the inflammation is transformed into chronic gastritis. In patients suffering from chronic gastritis, in 70 to 90% a *Helicobacter pylori* infection can be established (Calam, J (1994) *Helicobacter pylori* (Review) Eur. J. Clin Invest 24: 501-510). As *Helicobacter pylori* infection and chronic gastritis in the stomach are closely associated, it has been stipulated that this bacterial infection could be one etiological factor in the development of stomach cancer. It is for this reason possible that eradication of the *Helicobater pylori* bacteria in the initial stages of the infection, could prevent the development of atrophy associated with chronic gastritis, and thus reduce the cancer risk and the risk of peptic ulcers.

The publication WO 96/15456, which is included herein for reference, discloses a method for screening for the risk of cancer by determining the concentration of the analytes pepsinogen I and gastrin-17 from a serum sample of a subject. According to the said publication, the so determined concentration values are then compared to a cut-off value and a reference value for each analyte. A serum pepsinogen I concentration below the cut-off value for pepsinogen I in combination with a gastrin-17 concentration value above the upper reference limit indicates severe atrophy of the corpus area of the stomach. A serum gastrin-17 level below the cut-off value for gastrin-17 in combination with a pepsinogen I value above the cut-off value for pepsinogen I on the other hand indicates atrophy of the antrum area of the stomach. In case the serum pepsinogen I is below the cut-off value for pepsinogen I and the gastrin-17 level is at the lower limit of its reference value, this is an indication of severe atrophy in the whole stomach, i.e. of atrophic pangastritis.

According to an embodiment disclosed, the said tests may be combined with a test for *Helicobacter pylori* antibodies.

According to the said WO-publication, the method can be supplemented with a so-called protein stimulation test, according to which a blood sample is taken in the morning after fasting, whereafter the patient eats a protein-rich standard meal and blood samples are taken at 15 minute intervals for two hours. The maximal increase is evident after appr. 20 minutes. In case the atrophy is located in the antrum, there will be a strongly reduced response in this test. When the atrophy is located in the corpus, the response will be normal or increased, whereas atrophy of the whole mucosa leads to a reduced response.

The WO-publication WO 00/67035, which is included herein for reference, discloses a method for assessing the risk of peptic ulcer by determining quantitatively the concentration of serum pepsinogen I and serum gastrin-17. According to this method, if both the measured pepsinogen I and gastrin-17 values are high, above the upper limit of their respective reference values, or the serum pepsinogen I value is above the upper limit of its reference value in combination with a gastrin-17 value within the reference range or below its cut-off value, this is an indication of an increased risk of peptic ulcer.

Methods are known in the art for measuring the concentrations of the various analytes, and there are also commercially available kits for this purpose. Some exemplary methods for carrying out the said determinations are described in the WO-publication 96/15456 as well.

SUMMARY OF THE INVENTION

The object of the invention is a method for assessing the state of the gastric mucosa, especially for diagnosing mucosal gastric changes, such as atrophic gastritis, in a subject, by assaying the analytes pepsinogen I (PGI), gastrin and a marker for *Helicobacter pylori* infection, the method comprising measuring from a sample of said subject the pepsinogen I and gastrin concentration, and, in addition, determining the concentration or presence of a marker for *Helicobacter pylori* (Hp-marker), and entering the data so obtained for said analytes in a data processing means comprising an operating system, means for transceiving and processing data, said data processing means being adapted to perform the steps of comparing a measured concentration value for an analyte to a predetermined cut-off value for said analyte, to obtain a combination of comparison results which is specific for the subject tested, and generating information in response to the said combination of comparison results, and optionally other data entered.

The data processing means can comprise a display on which the generated information is displayed. The generated information advantageously relates to a diagnosis or a suggestion for treatments or further investigations and/or tests based on the comparison result obtained.

The invention is also directed to a kit and to a computer program product especially for use in the method according to the invention.

The invention is also directed to a kit comprising means for measuring, from a sample, the pepsinogen I and/or gastrin concentration, and/or means for determining the concentration or presence of a *Helicobacter pylori* marker, as well as a computer program product embodied on a computer readable medium and comprising computer code means adapted to perform the steps of comparing a measured concentration value of an analyte to a predetermined cut-off value for said analyte, combining the results of comparison to a combination of comparison results, and providing information in response to said combination and optionally to other entered data, when run on a computer.

Yet another object of the invention is a computer program product embodied on a computer readable medium and comprising computer code means adapted to perform the steps of comparing measured concentrations of an analyte to a respective cut-off value for said analyte, combining the results of comparison to a combination of comparison results, and providing information in response to said combination and optionally to other entered data, when run on a computer.

DETAILED DESCRIPTION OF THE INVENTION

The process of comparing the measured value to a cut-off value of an analyte is aimed at establishing if the measured value of the analyte is greater than, equal to or smaller than the respective cut-off value, and thus to generate specific combinations of comparison results for the analytes, based on which combination specific information will be generated and for example displayed on a display.

Thus according to the invention, for each subject to be tested, the data processing means generate a specific set of comparison results, which set is obtained by comparing a measured value to a predetermined cut-off value for the analytes, in any given order, or simultaneously. In the context of the invention, a subject means a mammal, such as a human, or an animal, such as a pet, e.g. a dog.

The present invention thus includes in a first step a method for determining at least a *Helicobacter pylori* marker, pepsinogen I (PGI) and gastrin.

The marker or indicator for *Helicobacter pylori* infection can thus, according to the invention, be for example a *Helicobater pylori* antibody, the value of which can be measured from a body fluid sample. Such a sample is advantageously a serum sample, but can also be a saliva, urine or lacrimal fluid sample, e.g. commercial kits being available for measuring the antibody value. The cut-off value for *Helicobacter pylori* antibodies can easily be defined by a person skilled in the art. In one embodiment of this invention we have used a value of 30 EIU as a cut-off for indicating the presence or absence of a *Helicobacter pylori* infection. Specific antibodies to *Helicobacter pylori* can also be measured using western blot.

Another alternative is to evaluate the presence of a *Helicobater pylori* infection by determining the presence of the antigen itself. Such measurement can for example be carried out on a stool sample from a patient, and assays, such as enzyme immunoassays are commercially available for this purpose (cf. for example Lancet 1999; 354, 30-33). It is also possible to determine the presence of the antigen from the breath of a patient, using the well known techniques of measuring the carbon dioxide content, the formation of which from labeled urea is catalyzed by *Helicobacter pylori* bacteria, and systems for this assay are also commercially available (e.g. Heliprobe™ by Noster AB, Sweden). Another alternative is to determine the presence of the antigen in a biopsy sample taken during endoscopy from the stomach of a paint. In this alternative the tests are either positive or negative for antigen, and a presence of antigen is taken as being indicative of a *Helicobacter pylori* infection. The result of the test is suitably entered in the data processing system as a boolean parameter.

Pepsinogen and gastrin are preferably determined from a body fluid sample, especially from a serum sample, or from a urine, salivary, or lacrimal fluid sample.

The method includes measuring the pepsinogen I analyte, but according to an embodiment of the invention it is also possible the measure, in addition, the concentration of the pepsinogen II analyte (PGII), and using the ratio PGI to PGII instead of PGI, or in addition thereto as the value to be compared to a predetermined cut-off value. Pepsinogen I and also the ratio of pepsinogen I to II tend to decrease linearly with worsening of the atrophy of the corpus mucosa.

In the method according to the invention a first lower cut-off value for pepsinogen I is typically used, which is the 'normal' cut-off value for differentiating between normal and atrophic corpus mucosa. In addition a second higher cut-off value for pepsinogen I can be used, such higher value, when the gastrin concentration is in its cut-off range indicating only slightly stimulated gastrin activity, defining the cut-off between a non-atrophic (incl. corpus) gastritis (pepsinogen I above second cut-off), and only mildly atrophic corpus mucosa (pepsinogen I below second cut-off) in combination with antrum atrophy. The said second cut-off value can easily be determined by the person skilled in the art.

The concentration of gastrin, and especially of gastrin-17, likewise decreases with worsening of the atrophy of the antrum mucosa. For gastrin, a cut-off range can be used. This range has a lower cut-off limit, values below which indicate atrophy of at least the antrum, as well as an upper cut-off limit, values above which can indicate normal, non-atrophic gastritis or an atrophic corpus mucosa. Values in the range between the lower and the upper value can indicate atrophy at least in the antrum area, or, in combination with a high pepsinogen value (above the second higher cut-off value), also non-atrophic gastritis, as discussed above. In addition, a third cut-off value, a lowest cut-off value for gastrin can be applied for indicating a normal mucosa when pepsinogen I is equal to or above its first cut-off value.

The gastrin analyte can be total gastrin, that is essentially the sum of gastrin-34 and gastrin-17, but according to a preferred embodiment of the invention, gastrin-17 is measured.

As mentioned earlier, the methods for measuring pepsinogen I, pepsinogen II and and gastrin are well known in the art. The measurements are usually immunological methods, using mono- or polyclonal antibodies to the said analytes. The detection methods for use include, for example, measuring absorbance, fluoresence or luminescence. It is also possible to carry out all three analyte measurements simultaneously, for example on the same microplate, in different wells or in the same well thereon, which provides for al especially convenient method.

The analyte values so obtained are then entered in a data processing means, such as a data terminal, which has the necessary operating system and which can be provided with means for data input and data output and which comprises means for comparing a measured analyte concentration to a predetermined cut-off value for the analyte. The data can be entered using any data terminal equipment with a proper user interface (UI) or by reading data from a data carrying and storing medium, or by receiving data from a data providing system, via data transmission means and data communication networks, such as internet.

The user interface is thus the means by which the user can communicate with the information providing system, and by means of which data is entered, validated and whereto generated information is reported or displayed, or for further transmission, for storage, or to be printed on a printer.

The concept of cut-off values in assays involving the determination of analyte concentrations is well known to the person skilled in the art, and it generally means a value or a set of values chosen as a limit between the reference values (normal values) and the abnormal values for the test in question. Such cut-off values are method-specific and depend on the specifity and sensitivity chosen for the test method used for the determination of the analyte concentrations, see for example William J Marshall, Clinical Chemistry, Third Edition, 1995, Mosby.

The cut-off values can be entered into the data processing system prior to entering the measured analyte values, or they can be pre-stored in the data processing system. According to the invention it is also contemplated to modify the cut-off values when carrying out the method, in case it is desired change the sensitivity or specificity of the method.

According to the invention the data processing means perform a comparison operation, according to which the various analyte concentrations measured are compared to a respective cut-off value or cut-off range for said analyte, the comparison results obtained are combined, and information in response to the said combination of comparison results and optionally to other or additional data or parameters entered in the data processing means, is generated, which information can be displayed for example on a display on the user interface.

Information created by the data processing means can take the form of a diagnosis displayed in a window on a display, or it can take the form of suggestions for treatment, or suggestions for further investigations or tests, displayed in the same or in a different display window.

Thus in accordance with the invention, depending on the specific combination of comparison results obtained, a main diagnosis can refer to 'normal (mucosa)', 'atrophic corpus gastritis' (optionally of autoimmune type), 'atrophic antrum and corpus gastritis' (pangastritis), 'atrophic antrum gastritis', or 'non-atrophic gastritis, supplemented with information relating to the presence or absence of a *Helicobacter pylori* infection.

The following Table includes specific combinations of comparison results associated with the different diagnoses, when the analytes are Hp-marker, such as a Hp-antibody, pepsinogen I and gastrin.

In the Table,
Hp-co means the cut-off value for the Hp marker
P-coI means the first cut-off for pepsinogen I
P-coII means the second cut-off value for pepsinogen I
G-coI means the lower cut-off value for gastrin
G-coII means the upper cut-off value for gastrin.

| Diagnosis | Hp-marker | PGI | gastrin |
|---|---|---|---|
| Normal | ≦Hp-co | ≧P-coI | any |
| Atrophic corpus gastritis | ≦Hp-co | ≧P-coI | >G-coII |
| Atrophic antrum/corpus gastritis | ≦Hp-co | <P-coI | <G-coI |
| Atrophic antrum/corpus gastritis | >Hp-co | <P-coI | <G-coI |
| Atrophic antrum gastritis | >Hp-co | ≧P-coI | <G-coI |
| Atrophic antrum gastritis | >Hp-co | <P-coII | G-coI–G-coII |
| Non-atrophic gastritis | >Hp-co | ≧P-coII | G-coI–G-coII |
| Non-atrophic gastritis | >Hp-co | ≧P-coI | >G-coII |
| Atrophic corpus gastritis | >Hp-co | <P-coI | >G-coII |

From the Table it can be seen that the *Helicobacter pylori* marker divides the set of specific combinations into two groups, wherein the measured Hp marker analytes are either above or below the cut-off value for the Hp marker (Hp-co). When the Hp-marker value is equal to or below the cut-off, a PGI value equal to or above the first PG cut-off value (P-coI) indicates a normal mucosa, whereas if the PGI value is below the said cut-off, a gastrin value equal to or above the upper cut-off limit for gastrin (G-coII) indicates atrophic corpus gastritis, whereas if this value is below the said cut-off, atrophic antrum/corpus gastritis, i.e. pangastritis is indicated. Instead of the provision of 'any value' for gastrin in the diagnosis of a normal mucosa, one can also apply a third lowest cut-off value for gastrin (G-coIII) above which the gastrin concentration should be to indicate a normal mucosa.

On the other hand, when the Hp-value is above its cut-off value, and the gastrin value is below its lower cut-off limit (G-coI), the indication is pangastritis if also the pepsinogen I is below its first cut-off, and the indication is atrophic antrum gastritis if the pepsinogen I is equal to or above its first cut-off. If the gastrin value is in the cut-off range (G-coI-G-coII), and the pepsinogen I is below its second cut-off value (P-coII) the indication is also atrophic antrum gastritis, but when the pepsinogen I is equal to or above its second cut-off, the indication is non-atrophic gastritis. Finally, when the gastrin is above the upper cut-off limit (G-coII), and the pepsinogen I is equal to or above the first cut-off, non-atrophic gastritis is indicated, but when the pepsinogen is below the first cut-off, atrophic corpus gastritis is indicated. In the above Table, when the presence of a Hp marker, such as the antigen, rather than the antibody concentration is determined, the table includes only the options of presence or absence of antigen in the sample.

The above mentioned diagnoses can further be supplemented with information relating to a risk of developing peptic ulcer (gastric and/or duodenal) as well as the associated risk factor therefore, as well as a possible risk of cancer, and its associated risk factor. The criteria for establishing the risk of peptic ulcer and of cancer based on the measured PGI and G-17 values as compared to their cut-off and reference values, have been described in the WO 00/67035 and WO 96/15456 respectively. The different risk factors associated with peptic ulcer and cancer have been described in detail for example in Gastroenterology Clinics of North America, Volume 29, No. 3 (2000), reference being made especially to page 586, where the various risk factors associated with normal, non-atrophied, mild, moderate and severe atrophy of the antrum and corpus mucosa are disclosed both for peptic ulcer and cancer, in diagram form.

Further optional parameters that can be taken into account, when creating the information for display for example in the form of a diagnosis, can be the age of the patient, a condition of e.g. reflux symptoms, dyspepsia, and/or anemia, or also other symptoms and disease states, whereby, according to an embodiment of the invention, the mentioned sympoms or diseases can be entered into the data processing means as boolean parameters.

The Table disclosed above can be supplemented, for example, with a cut-off value for age, whereby, for example, an age over 45 years in combination with dyspepsia in patients with a *Helicobacter pylori* infection and a non-atrophic gastritis or atrophic corpus gastritis can, in addition to the diagnosis relating to the state of the gastric mucosa, prompt a suggestion to treat the patient for *Helicobacter pylori* infection.

Furthermore, for example a diagnosis of atrophic corpus gastritis optionally in combination with pernicious anemia irrespective of age could prompt a suggestion for testing for vitamin B12 and homocysteine from the serum, and possibly also a suggestion for B12 vitamin supplementation treatment.

The invention is also directed to a kit comprising means for measuring, from a sample, the pepsinogen I and/or gastrin concentration, and/or means for determining the concentration or presence of a *Helicobacter pylori* marker. The kit thus contains the various means, such as reagents, needed for measuring the concentration or presence of the analyte in question, packed in different containers but contained in the same package. The kit also can contain instructions of use. In addition the kit contains a computer program product embodied on a computer readable medium and comprising computer code means, which when run on a computer, are adapted to perform the steps of comparing the measured concentration values of an analyte with its predetermined cut-off value to provide the combination of comparison results, which together with optionally other data entered forms the basis for the information to be generated when used on a computer. The computer program product can contain pre-stored cut-off values for one or more of the analytes to be measured, or such values can be entered at the time of use. When using the kit, the concentration of the at least one analyte, as well as the concentrations of any of the other analytes as required, measured with the same kit or using other means or kits, are entered when using the program on a computer.

Yet another object of the invention is a computer program product embodied on a computer readable medium and comprising computer code means adapted to perform the steps of comparing the measured concentration values of an analyte, such as the analytes Hp-marker, PGI and gastrin, with its predetermined cut-off value, to provide combinations of comparison results to generate, optionally with other data entered, information, when run on a computer.

Figure 1:
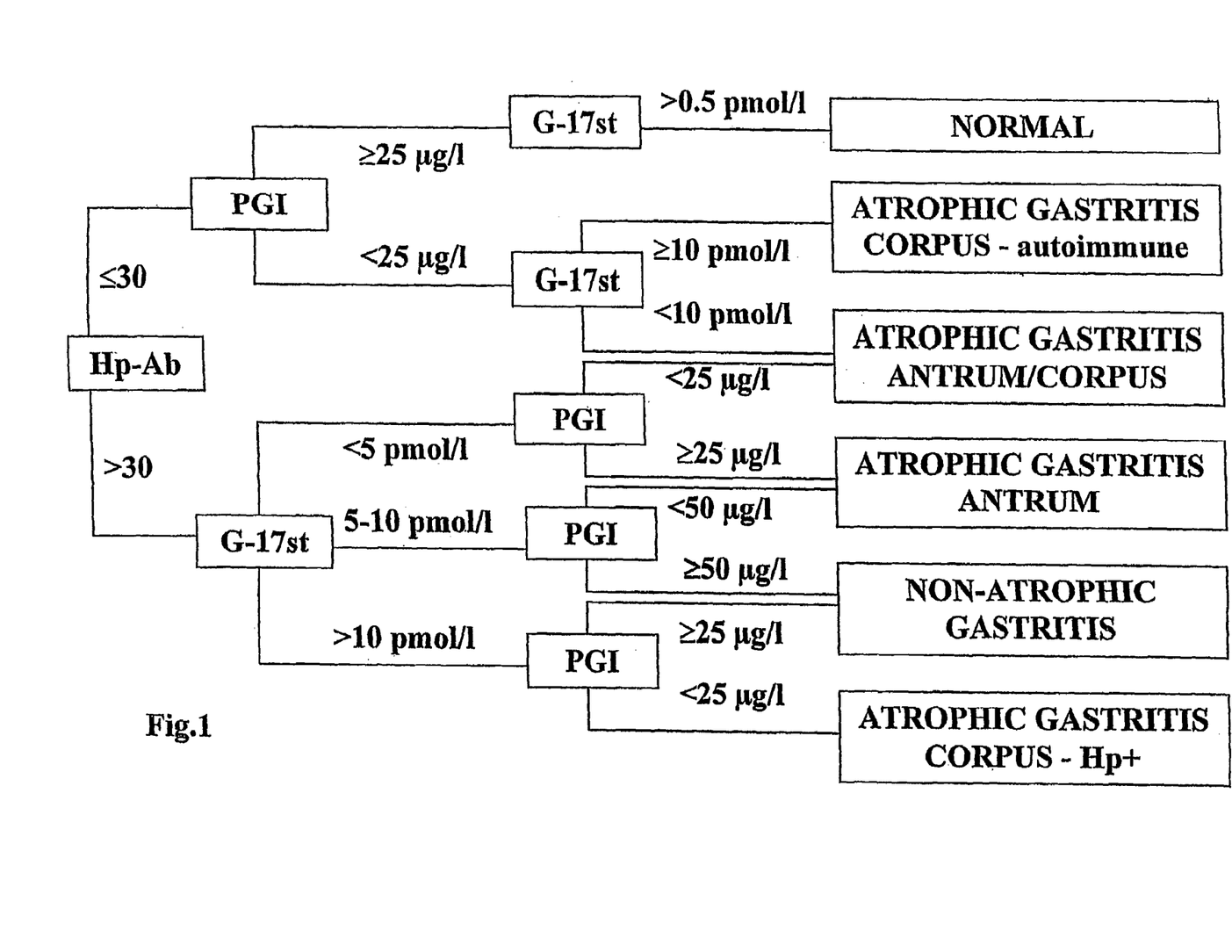

Reference is made to the enclosed FIG. 1, wherein a diagram referring to a test panel or 'decision tree' according to an embodiment of the invention is disclosed. The cut-off values for each one of the analytes are those indicated in the diagram and referred to below, which have shown to give accurate diagnoses for the average population. Naturally it is possible to use also other or more or less modified cut-off values, should the methods used for the determination of the analyte concentrations, and/or the sensitivity and specificity so require.

The sample used is a serum sample, and the gastrin is gastrin-17 (G-17). In the determination of serum pepsinogen I the cut-off-value for atrophic gastritis is, according to our previous studies, 20-30 µg/l depending on the specificity and sensitivity agreed upon for the method in question, which corresponds to appr. 450-690 pmol/l. In this example we have used a value of 25 µg/l as the first cut-off value for atrophic gastritis in the corpus area or atrophic pangastritis. However, according to the invention it is possible to use also a second value for PGI as a cut-off value to distinguish between atrophic gastritis in the antrum (with only mild atrophic corpus gastritis) and non-atrophic gastritis, respectively, when the G-17 is within the cut-off range for G-17. In the context of this invention, this second value is termed the second cut-off value. In this example we have used a value of 50 µg/l for this second cut-off value, a value appr. twice that of the first cut-off value. If the pepsinogen II analyte concentration is measured in addition, the first cut-off value for the ratio of PGI to PGII can be for example 2.5, and the second cut-off for example appr. 5.

In this example we use the serum gastrin-17 concentration obtained after protein stimulation, i.e. the postprandial gastrin-17. The cut-off range for 'stimulated' gastrin-17 (G-17st) is normally in the range of 5 to 10 pmol/l, whereby the lower limit of 5 pmol/l forms a lower cut-off value, the upper limit of 10 pmol/l the upper cut-off value, and the intermediate range a third cut-off range. In addition there is a lowest cut-off for gastrin-17 of 0.5 pmol/l which is applicable for indicating a normal mucosa with normal PGI values (PGI≧25 μg/l). The corresponding values and ranges for unstimulated G-17 would be approximately half of those given for the stimulated values. In this example we have used the *Helicobacter pylori* antibodies as a Hp-marker, and we have found that a suitable cut-off value for the *Helicobacter pylori* antibody value is appr. 30 EIU.

According to the embodiment described in this example, the data processing means carries out a comparison of the measured Hp-Ab value to the cut-off value for Hp-Ab, which is indicated as being 30 EIU. Depending on the measured value being higher than, or equal to or lower than the predetermined cut-off value, the data processing means perform in the first case a comparison of the measured G-17st to is its cut-off range, and in the later case the data processing means perform a comparison of PGI to its first cut-off value.

If, in the first case, the G-17st is either below the lower cut-off value, or above its higher cut-off value, the data processing means perform a comparison of the PGI to its said first cut-off value. When G-17st is below its lower cut-off and the PGI is below its first cut-off value, the data processing system will generate information relating to a diagnosis of atrophic antrum and corpus gastritis (pangastritis), but if the PGI is equal to or higher than the first cut-off value, the information will relate to atrophic gastritis of the antrum.

When G-17st is above its upper cut-off and the PGI is below the fist cut-off value for PGI, the information generated will relate to atrophic gastritis of the corpus, but if the measured PGI is equal to or above the first cut-off value for PGI, the information generated will relate to non-atrophic gastritis. The same diagnosis will be displayed if the measured PGI is high, and equal to or higher than the second cut-off value for PGI in combination with a G-17st in the cut-off range. If in turn, the measured PGI is below the second cut-off value for PGI, with G-17st in the cut-off range, the diagnoses displayed will be atrophic gastritis of the antrum area.

On the other hand, if the Hp-Ab value is lower than or equal to its cut-off value, the data processing means perform a comparison of the measured PGI value with the first cut-off value for PGI. In case the measured PGI value is equal to or higher than the said cut-off value, the information generated will refer to a diagnosis of a normal mucosa at a gastrin-17st value above the third lowest cut-off which in this example is 0.5 pmol/l. However, if the said measured PGI value is below the first cut-off value, the information displayed will relate to a diagnosis of atrophic corpus gastritis when the measured G-17st is equal to or higher than the upper cut-off value, and to a diagnosis of pangastritis, when also the G-17st is low, namely below the upper cut-off limit. The atrophic corpus gastritis will in this case be of the autoimmune type.

As stated earlier, by feeding additional parameters into the data processing system, and combining them with the generated information, it is possible to provide additional information, for example in the form of suggestions for further treatments and/or further investigations, such as a suggestion to undergo endoscopy, to determine B12 vitamin and homocysteine levels, and eradication treatment of *Helicobacter pylori* infection.

The following examples are intended to illustrate the invention without restricting it in any way. The analytes measured are serum pepsinogen I, serum gastrin-17 and *Helicobacter pylori* antibodies; the cut-off values are those shown in FIG. 1. Also the age of the patient has been included as a parameter, the cut-off being 45 years. The respective diagnosis is given in each example, together with further suggestions for examinations and treatments, when applicable.

EXAMPLE 1

| | |
|---|---|
| Serum pepsinogen I | 30 μg/l |
| Serum gastrin-17st | 20 pmol/l |
| *Helicobacter pylori* antibodies | 10 EIU |
| Patient's age | 40 years |

Suggested diagnosis: NORMAL
1) No atrophic gastritis
2) No *H. pylori* infection
3) No risk of gastric cancer and peptic ulcer diseases (duodenal and gastric); risk factor 1×
Suggested further investigation and treatment:
No further examinations (e.g. endoscopy) recommended.

EXAMPLE 2

| | |
|---|---|
| Serum pepsinogen I | 20 μg/l |
| Serum gastrin-17st | 20 pmol/l |
| *Helicobacter pylori* antibodies | 10 EIU |
| Patient's age | 40 years |

Suggested diagnosis: ATROPHIC CORPUS GASTRITIS
1) Peptic ulcer disease (duodenal and gastric ulcer) unlikely
2) Autoimmune type atrophic corpus gastritis
3) Increased risk of gastric cancer (risk factor 3-5×
Suggested further investigation and treatment:
Endoscopy advisable. Vitamin B12 and homocysteine determination recommended.
Vitamin B12 replacement therapy, if B12 below 170 pmol/l.

EXAMPLE 3

| | |
|---|---|
| Serum pepsinogen I | 20 μg/l |
| Serum gastrin-17st | 5 pmol/l |
| *Helicobacter pylori* antibodies | 10 EIU |
| Patient's age | 40 years |

Suggested diagnosis: ATROPHIC ANTRUM/CORPUS GASTRITIS
1) Peptic ulcer disease (duodenal and gastric) unlikely
2) Increased risk of gastric cancer (risk factor 3-90×)
Suggested further investigation and treatment:
Endoscopy advisable. Vitamin B12 and homocysteine determination recommended.

Vitamin B12 replacement therapy, if B12 below 170 pmol/l.

EXAMPLE 4

| | |
|---|---|
| Serum pepsinogen I | 20 µg/l |
| Serum gastrin-17st | 2 pmol/l |
| *Helicobacter pylori* antibodies | 80 EIU |
| Patient's age | 40 years |

Suggested diagnosis: ATROPHIC ANTRUM/CORPUS GASTRITIS
1) Peptic ulcer disease (duodenal and gastric) unlikely
2) Increased risk of gastric cancer (risk factor 3-90×)
Suggested further investigation and treatment:
Endoscopy advisable. Vitamin B12 and homocysteine determination recommended.
Vitamin B12 replacement therapy, if B12 below 170 pmol/l. Treatment of *H. pylori* infection necessary.

EXAMPLE 5

| | |
|---|---|
| Serum pepsinogen I | 30 µg/l |
| Serum gastrin-17st | 2 pmol/l |
| *Helicobacter pylori* antibodies | 80 EIU |
| Patient's age | 40 years |

Suggested diagnosis: ATROPHIC ANTRUM GASTRITIS
1) High risk of peptic ulcer disease (duodenal and gastric) (risk factor 10-20×)
2) Increased risk of gastric cancer (risk factor 18×)
Suggested further investigation and treatment:
Endoscopy advisable. Treatment of *H. pylori* infection necessary.

EXAMPLE 6

| | |
|---|---|
| Serum pepsinogen I | 30 µg/l |
| Serum gastrin-17st | 8 pmol/l |
| *Helicobacter pylori* antibodies | 80 EIU |
| Patient's age | 40 years |

Suggested diagnosis: ATROPHIC ANTRUM GASTRITIS
1) High risk of peptic ulcer disease (duodenal and gastric) (risk factor 10-20×)
2) Increased risk of gastric cancer (risk factor 18×)
Suggested further examination and treatment.
Endoscopy advisable. Treatment of *H. pylori* infection necessary.

EXAMPLE 7

| | |
|---|---|
| Serum pepsinogen I | 60 µg/l |
| Serum gastrin-17st | 8 pmol/l |
| *Helicobacter pylori* antibodies | 80 EIU |
| Patient's age | 40 years |

Suggested diagnosis: NON-ATROPHIC GASTRITIS
1) Increased risk of peptic ulcer disease (duodenal and gastric) (risk factor 10×)
2) Low risk of gastric cancer (risk factor 1-2×)
Suggested further investigation and treatment:
Endoscopy not necessary. Treatment of *H. pylori* infection necessary.

EXAMPLE 8

| | |
|---|---|
| Serum pepsinogen I | 50 µg/l |
| Serum gastrin-17st | 20 pmol/l |
| *Helicobacter pylori* antibodies | 80 EIU |
| Patient's age | 40 years |

Suggested diagnosis: NON-ATROPHIC GASTRITIS
1) Increased risk of peptic ulcer disease (duodenal and gastric) (risk factor 10×)
2) Low risk of gastric cancer (risk factor 1-2×)
Suggested further investigation and treatment:
Endoscopy not necessary. Treatment of *H. pylori* infection necessary.

EXAMPLE 9

| | |
|---|---|
| Serum pepsinogen I | 20 µg/l |
| Serum gastrin-17st | 20 pmol/l |
| *Helicobacter pylori* antibodies | 80 EIU |
| Patient's age | 40 years |

Suggested diagnosis: ATROPHIC CORPUS GASTRITIS
1) Increased risk of gastric cancer (risk factor 3-5×)
Suggested further investigation and treatment:
Endoscopy advisable. Vitamin B12 and homocysteine determination recommended.
Vitamin B12 replacement therapy, if B12 below 170 pmol/l. Treatment of *H. pylori* infection.

EXAMPLE 10

| | |
|---|---|
| Serum pepsinogen I | 50 µg/l |
| Serum gastrin-17 st | 20 pmol/l |
| *Helicobacter pylori* antibodies | 80 EIU |
| Patient's age | 50 years |

Suggested diagnosis: NON-ATROPHIC GASTRITIS
1) Increased risk of peptic ulcer disease (duodenal and gastric) (risk factor 10×)
2) Low risk of gastric cancer (risk factor 1-2×)
Suggested further investigation and treatment:
Endoscopy advisable. Treatment of *H. pylori* infection if dyspeptic symptoms.

EXAMPLE 11

| | |
|---|---|
| Serum pepsinogen I | 20 µg/l |
| Serum gastrin-17 st | 20 pmol/l |
| *Helicobacter pylori* antibodies | 80 EIU |
| Patient's age | 50 years |

Suggested diagnosis: ATROPHIC CORPUS GASTRITIS

1) Increased risk of gastric cancer (risk factor 3-5×)

Suggested further investigation and treatment:

Endoscopy advisable. Vitamin B12 and homocysteine determination recommended.

Vitamin B12 replacement therapy, if B12 below 170 pmol/l. Treatment of *H. pylori* infection necessary if dyspeptic symptoms.

| PGI | G17 or stG17 | HP-Marker | Diagnosis |
|---|---|---|---|
| ≧20-30 µg/l | Any | ≦30 EIU | Normal |
| <20-30 µg/l | ≧10 pmol/l stG17 or ≧5 pmol/l G17 | ≦30 EIU | Atrophic corpus gastritis |
| <20-30 µg/l | <10 pmol/l stG17 or <5 pmol/l G17 | ≦30 EIU | Atrophic antrum/corpus gastritis |
| <20-30 µg/l | <5 pmol/l stG17 or <2.5 pmol/l G17 | >30 EIU | Atrophic antrum/corpus gastritis |
| ≧20-30 µg/l | <5 pmol/l stG17 or <2.5 pmol/l G17 | >30 EIU | Atrophic antrum gastritis |
| <50 µg/l | 5-10 pmol/l stG17 or 2.5-5 pmol/l G17 | >30 EIU | Atrophic antrum gastritis |
| ≧50 µg/l | 5-10 pmol/l stG17 or 2.5-5 pmol/l G17 | >30 EIU | Non-atrophic gastritis |
| ≧20-30 µg/l | >10 pmol/l stG17 or >5 pmol/l G17 | >30 EIU | Non-atrophic gastritis |
| <20-30 µg/l | >10 pmol/l stG17 or >5 pmol/l G17 | >30 EIU | Atrophic corpus gastritis |

The invention claimed is:

1. A method for assessing the condition of the gastric mucosa in a subject to diagnose gastric mucosa conditions selected from the group consisting of atrophic corpus gastritis, atrophic antrum gastritis, atrophic antrum/corpus gastritis and non-atrophic gastritis by assaying (i) pepsinogen I (PGI), (ii) unstimulated gastrin-17 (G17) or stimulated gastrin 17 (stG17) and (iii) a marker for Helicobacter pylon infection (Hp-Marker), the method comprising:

(1) obtaining a serum, urine, saliva or lacrimal fluid sample from said subject;
   (2) quantitatively measuring the concentration of PGI in said sample from step (1);
   (3) quantitatively measuring the concentration of G17 or stG17 in said sample from step (1);
   (4) determining
      a value for said Hp-marker by quantitatively measuring the enzyme immunoassay units (EIU) value of an *Helicobacter pylori* (Hp) antibody in said sample from step (1);, and
   (5) entering into a data processing system comprising a data storing means or a data display the PGI concentration, the G17 or stG17 concentration and the EIU value of the Hp antibody, wherein said data processing system comprises computer code which, when executed on a computer, performs the steps comprising:
      (a) comparing said PGI concentration to a low PGI cut-off value (PGI-coI) of 20-30 µg/l and a high PGI cut-off value (PGI-coII) of 50 µg/l to obtain a PGI comparison result,
      (b) comparing said G17 concentration to a low G17 cut-off value (G17-coI) of 2.5 pmol/l and a high G17 cut-off value (G17-coII) of 5 pmol/l to obtain a G17 comparison result or comparing said stG17 concentration to a low stG17 cut-off value (stG17-coI) of 5 pmol/l and a high G17 cut-off value (stG17-coII) of 10 pmol/l to obtain a stG17 comparison result,
      (c) comparing said Hp antibody value to an Hp antibody cut-off (Hp-co) value of 30 EIU to obtain an antibody HP-marker comparison result, and
      (d) combining the comparison results of steps 5(a), 5(b) and 5(c) to generate diagnosis information for the gastric mucosa condition of said subject according to the following table:

and stores or displays said diagnosis information, and (6) using said stored or displayed diagnosis information to diagnose in said subject a normal gastric mucosa condition or one or more gastric mucosa conditions selected from the group consisting of atrophic corpus gastritis, atrophic antrum/corpus gastritis, atrophic antrum gastritis and non-atrophic gastritis.

2. A method for assessing the condition of the gastric mucosa in a subject to diagnose gastric mucosa conditions selected from the group consisting of atrophic corpus gastritis, atrophic antrum gastritis, atrophic antrum/corpus gastritis and non-atrophic gastritis by assaying (i) pepsinogen I (PGI), (ii) unstimulated gastrin-17 (G17) or stimulated gastrin 17 (stG17) and (iii) a marker for *Helicobacter pylori* infection (Hp-Marker), the method comprising:

(1) obtaining a serum, urine, saliva or lacrimal fluid sample from said subject;
   (2) obtaining a stool, breath or biopsy sample from said subject;
   (3) quantitatively measuring the concentration of PGI in said sample from step (1);
   (4) quantitatively measuring the concentration of G17 or stG17 in said sample from said step (1);
   (5) determining the presence or absence of an Hp antigen in said sample obtained from said subject in step (2), and
   (6) entering into a data processing system comprising a data storing means or a data display the PGI concentration, the G17 or stG17 concentration and the presence or absence of the Hp antigen, wherein said data processing system comprises computer code which, when executed on a computer, performs the steps comprising:
      (a) comparing said PGI concentration to a low PGI cut-off value (PGI-coI) of 20-30 µg/l and a high PGI cut-off value (PGI-coII) of 50 µg/l to obtain a PGI comparison result,
      (b) comparing said G17 concentration to a low G17 cut-off value (G17-coI) of 2.5 pmol/l and a high G17 cut-off value (G17-coII) of 5 pmol/l to obtain a G17 comparison result or comparing said stG17 concentration to a low stG17 cut-off value (stG17-coI) of 5 pmol/l and a high G17 cut-off value (stG17-coII) of 10 pmol/l to obtain a stG17 comparison result , and
      (c) combining the comparison results of steps 6(a), 6(b) and the presence or absence of the HP marker to generate diagnosis information for the gastric mucosa condition of said subject according to the following table:

| PGI | G17 or stG17 | HP-Marker | Diagnosis |
|---|---|---|---|
| ≧20-30 µg/l | Any | Absent | Normal |
| <20-30 µg/l | ≧10 pmol/l stG17 or ≧5 pmol/l G17 | Absent | Atrophic corpus gastritis |
| <20-30 µg/l | <10 pmol/l stG17 or <5 pmol/l G17 | Absent | Atrophic antrum/corpus gastritis |
| <20-30 µg/l | <5 pmol/l stG17 or <2.5 pmol/l G17 | Present | Atrophic antrum/corpus gastritis |
| ≧20-30 µg/l | <5 pmol/l stG17 or <2.5 pmol/l G17 | Present | Atrophic antrum gastritis |
| <50 µg/l | 5-10 pmol/l stG17 or 2.5-5 pmol/l G17 | Present | Atrophic antrum gastritis |
| ≧50 µg/l | 5-10 pmol/l stG17 or 2.5-5 pmol/l G17 | Present | Non-atrophic gastritis |
| >20-30 µg/l | >10 pmol/l stG17 or >5 pmol/l G17 | Present | Non-atrophic gastritis |
| <20-30 µg/l | >10 pmol/l stG17 or >5 pmol/l G17 | Present | Atrophic corpus gastritis |

(7) using said stored or displayed diagnosis information to diagnose in said subject a normal gastric mucosa condition or one or more gastric mucosa conditions selected from the group consisting of atrophic corpus gastritis, atrophic antrum/corpus gastritis, atrophic antrum gastritis and non-atrophic gastritis.

3. The method according to claim 1, further comprising:
(a) quantitatively measuring the concentration of pepsinogen II (PGII); and
(b) forming a PGI/PGII ratio,
wherein step (5) further comprises entering said PGI/PGII ratio into said data processing system, and wherein said data processing system further comprises the step of:
(5)(a') comparing said PGI/PGII ratio to a low PGI/PGII cut-off value (PGI/PGII-coI) of 2.5 µg/l and a high PGI/PGII cut-off value (PGI/PGII-co-II) of 5 µg/l to obtain a PGI/PGII combination comparison result, and wherein in step (5)(d) the comparison results of steps (5)(a), (5)(b) and (5)(c) are further combined with the comparison result of step (5)(a'), and wherein the diagnosis table is:

| PGI | PGI/PGII | G17 or stG17 | HP-Marker | Diagnosis |
|---|---|---|---|---|
| ≧20-30 µg/l | ≧2.5 | Any | ≦30 EIU | Normal |
| <20-30 µg/l | <2.5 | ≧10 pmol/l stG17 or ≧5 pmol/l G17 | ≦30 EIU | Atrophic corpus gastritis |
| <20-30 µg/l | <2.5 | <10 pmol/l stG17 or <5 pmol/l G17 | ≦30 EIU | Atrophic antrum/corpus gastritis |
| <20-30 µg/l | <2.5 | <5 pmol/l stG17 or <2.5 pmol/l G17 | >30 EIU | Atrophic antrum/corpus gastritis |
| ≧20-30 µg/l | ≧2.5 | <5 pmol/l stG17 or <2.5 pmol/l G17 | >30 EIU | Atrophic antrum gastritis |
| <50 µg/l | <5 | 5-10 pmol/l stG17 or 2.5-5 pmol/l G17 | >30 EIU | Atrophic antrum gastritis |
| ≧50 µg/l | ≧5 | 5-10 pmol/l stG17 or 2.5-5 pmol/l G17 | >30 EIU | Non-atrophic gastritis |
| ≧20-30 µg/l | ≧2.5 | >10 pmol/l stG17 or >5 pmol/l G17 | >30 EIU | Non-atrophic gastritis |
| <20-30 µg/l | <2.5 | >10 pmol/l stG17 or >5 pmol/l G17 | >30 EIU | Atrophic corpus gastritis. |

4. The method according to claim 1 or 2, further comprising
measuring both the unstimulated gastrin-17 and stimulated gastrin-17 concentrations.

5. The method according to claim 2, further comprising:
(a) quantitatively measuring the concentration of pepsinogen II (PGII); and
(b) forming a PGI/PGII ratio,
wherein step (6) further comprises entering said PGI/PGII ratio into said data processing system, and wherein said data processing system further comprises the step of:
(5)(a') comparing said PGI/PGII ratio to a low PGI/PGII cut-off value (PGI/PGII-coI) of 2.5 µg/l and a high PGI/PGII cut-off value (PGI/PGII-co-II) of S µg/l obtain a PGI/PGII combination comparison result, and wherein in step (6)(d) the comparison results of steps (6)(a), (6)(a') and (6)(b) are further combined with the presence or absence of said Hp antigen, and wherein the diagnosis table is:

| PGI | PGI/PGII | G17 or stG17 | HP-Marker | Diagnosis |
|---|---|---|---|---|
| ≧20-30 µg/l | ≧2.5 | Any | Absent | Normal |
| <20-30 µg/l | <2.5 | ≧10 pmol/l stG17 or ≧5 pmol/l G17 | Absent | Atrophic corpus gastritis |
| <20-30 µg/l | <2.5 | <10 pmol/l stG17 or <5 pmol/l G17 | Absent | Atrophic antrum/corpus gastritis |
| <20-30 µg/l | <2.5 | <5 pmol/l stG17 or <2.5 pmol/l G17 | Present | Atrophic antrum/corpus gastritis |
| ≧20-30 µg/l | ≧2.5 | <5 pmol/l stG17 or <2.5 pmol/l G17 | Present | Atrophic antrum gastritis |
| <50 µg/l | <5 | 5-10 pmol/l stG17 or 2.5-5 pmol/l G17 | Present | Atrophic antrum gastritis |

-continued

| PGI | PGI/PGII | G17 or stG17 | HP-Marker | Diagnosis |
|---|---|---|---|---|
| ≧50 µg/l | ≧5 | 5-10 pmol/l stG17 or 2.5-5 pmol/l G17 | Present | Non-atrophic gastritis |
| ≧20-30 µg/l | ≧2.5 | >10 pmol/l stG17 or >5 pmol/l G17 | Present | Non-atrophic gastritis |
| <20-30 µg/l | <2.5 | >10 pmol/l stG17 or >5 pmol/l G17. | Present | Atrophic corpus gastritis |

6. The method according to claim 1 or 2, wherein the sample obtained in step (1) is a serum sample.

7. The method according to claim 1 or 2, wherein the data processing system comprises a display, and the information generated is displayed on the display.

8. The method according to claim 1 or 2, wherein a diagnosis of said subject as having a gastric mucosa condition selected from the group consisting of atrophic corpus gastritis, atrophic antrum/corpus gastritis, atrophic antrum gastritis and non-atrophic gastritis further comprises a method of
   (a) therapeutic treatment comprising administering B-12 vitamin replacement therapy or administering *Helicobacter pylori* infection therapy; or
   (b) further investigation comprising carrying out endoscopy on said subject or evaluating said sample for at least one of B12 vitamin levels or homocysteine.

9. The method according to claim 1 or 2, wherein a diagnosis of atrophic corpus gastritis, atrophic antrum gastritis or atrophic antrum/corpus gastritis—indicates said subject is at risk for peptic ulcer and/or cancer disease.

10. The method according to claim 1 or 2, wherein step (5) further comprises entering into the data processing system additional data relating to the age, reflux symptoms, dyspepsia and/or anemia of the subject.

11. The method of claim 1 or 2, wherein the data processing system of step 5 further comprises a data storing means.

12. The method according to claim 11, further comprising the step of storing at least one member of the group consisting of said Hp antibody cut-off value, PGI low cut-off value, PGI high cut-off value, PGII cut-off value, G17 low cut-off value, G17 high cut-off value, stG17 low cut-off value, stG17 high cut-off value and Hp antigen status in said data storing means.

13. The method according to claim 1 or 2, wherein a diagnosis of said subject as having non-atrophic gastritis further comprises a method of
   (a) therapeutic treatment comprising administering B-12 vitamin replacement therapy or administering *Helicobacter pylori* infection therapy; or
   (b) further investigation comprising carrying out endoscopy on said subject or evaluating said sample for at least one of B12 vitamin levels or homocysteine.

14. A computer readable storage medium comprising computer code which when executed on a computer assesses the condition of the gastric mucosa in a patient by performing the steps comprising:

(a) comparing a quantitatively measured Pepsinogen I (PGI) concentration value to a low PGI cut-off value (PGI-coI) of 20-30 µg/l and a high PGI cut-off value (PGI-coII) of 50 µg/l to obtain a comparison result;
   (b) comparing a quantitatively measured G17 concentration to a low G17 cut-off value (G17-coI) of 2.5 pmol/l and a high G17 cut-off value (G17-coII) of 5 pmol/l to obtain a G17 comparison result or comparing a quantitatively measured stG17 concentration to a low stG17 cut-off value (stG17-coI) of 5 pmol/l and a high G17 cut-off value (stG17-coII) of 10 pmol/l to obtain a stG17 comparison result;
   (c) comparing a quantitatively measured Hp antibody value to an Hp antibody cut-off (Hp-co) value of 30 EIU to obtain an Hp antibody comparison result or assessing an entered Hp antigen status as positive or negative, and
   (d) combining the comparison results of steps (a), (b) and (c) or combining the comparison results of steps (a) and (b) and the antigen Hp-marker positive or negative status to generate diagnosis information for the gastric mucosa condition of said subject according to the following table:

| | | HP-Marker | | |
|---|---|---|---|---|
| PGI | G17 or stG17 | Antibody | Antigen | Diagnosis |
| ≧20-30 µg/l | Any | ≦30 EIU | Negative | Normal |
| <20-30 µg/l | ≧10 pmol/l stG17 or ≧5 pmol/l G17 | ≦30 EIU | Negative | Atrophic corpus gastritis |
| <20-30 µg/l | <10 pmol/l stG17 or <5 pmol/l G17 | ≦30 EIU | Negative | Atrophic antrum/corpus gastritis |
| <20-30 µg/l | <5 pmol/l stG17 or <2.5 pmol/l G17 | >30 EIU | Positive | Atrophic antrum/corpus gastritis |
| ≧20-30 µg/l | <5 pmol/l stG17 or <2.5 pmol/l G17 | >30 EIU | Positive | Atrophic antrum gastritis |

-continued

| | | HP-Marker | | |
|---|---|---|---|---|
| PGI | G17 or stG17 | Antibody | Antigen | Diagnosis |
| <50 µg/l | 5-10 pmol/l stG17 or 2.5-5 pmol/l G17 | >30 EIU | Positive | Atrophic antrum gastritis |
| ≧50 µg/l | 5-10 pmol/l stG17 or 2.5-5 pmol/l G17 | >30 EIU | Positive | Non-atrophic gastritis |
| ≧20-30 µg/l | >10 pmol/l stG17 or >5 pmol/l G17 | >30 EIU | Positive | Non-atrophic gastritis |
| <20-30 µg/l | >10 pmol/l stG17 or >5 pmol/l G17, | >30 EIU | Positive | Atrophic corpus gastritis | and (e) outputting as a result of said comparing steps diagnosis information for diagnosing a normal gastric mucosa condition or one or more gastric mucosa conditions selected from the group consisting of atrophic corpus gastritis, atrophic antrum/corpus gastritis, atrophic antrum gastritis and non-atrophic gastritis.

15. A method for assessing the condition of the gastric mucosa in a subject to diagnose a gastric mucosa condition of atrophic corpus gastritis by assaying pepsinogen I (PGI), unstimulated gastrin-17(G17) or stimulated gastrin-17 (stG17) and a marker for *Helicobacter pylori* infection (Hp-marker), the method comprising:

(1) obtaining a serum, urine, saliva or lacrimal fluid sample from said subject;

(2) quantitatively measuring the concentration of PGI in said sample from step (1);

(3) quantitatively measuring the concentration of G17 or stG17 in said sample from step (1);

(4) determining
a value for said Hp-marker by quantitatively measuring the enzyme immunoassay units (EIU) value of an *Helicobacter pylori* (Hp) antibody in said sample from step (1); and (5) entering into a data processing system comprising a data storing means or a display the PGI concentration, the G17 or stG17 concentration and the EIU value of the Hp antibody wherein said data processing system comprises computer code which, when executed on a computer, performs the steps comprising:

(a) comparing said PGI concentration to a low PGI cut-off value (PGI-coI) of 20-30 µg/l and a high PGI cut-off value (PGI-coII) of 50 µg/l to obtain a PGI comparison result, (b) comparing said G17 concentration to a low G17 cut-off value (G17-coI) of 2.5 pmol/l and a high G17 cut-off value (G17-coII) of 5 pmol/l to obtain a G17 comparison result or comparing said stG17 concentration to a low stG17 cut-off value (stG17-coI) of 5 pmol/l and a high stG17 cut-off value (stG17-coII) of 10 pmol/l to obtain a stG17 comparison result (c) comparing said Hp antibody value to an Hp antibody cut-off (Hp-co) value of 30 EIU to obtain an Hp antibody comparison result, and (d) combining the comparison results of steps 5(a), 5(b) and 5(c) to generate diagnosis information for the gastric mucosa of said subject according to the following table:

| PGI | G17 or stG17 | HP-Marker | Diagnosis |
|---|---|---|---|
| ≧20-30 µg/l | Any | ≦30 EIU | Normal |
| <20-30 µg/l | ≧10 pmol/l stG17 or ≧5 pmol/l G17 | ≦30 EIU | Atrophic corpus gastritis |
| <20-30 µg/l | >10 pmol/l stG17 or >5 pmol/l G17 | >30 EIU | Atrophic corpus gastritis | and stores or displays said diagnosis information, and (6) using said stored or displayed diagnosis information to diagnose in said subject the gastric mucosa condition of atrophic corpus gastritis.

16. A method for assessing the condition of the gastric mucosa in a subject to diagnose a condition of atrophic antrum/corpus gastritis by assaying pepsinogen I (PGI), unstimulated gastrin-17(G17) or stimulated gastrin-17 (stG17) and a marker for *Helicobacter pylori* infection (Hp-marker), the method comprising:

(1) obtaining a serum, urine, saliva or lacrimal fluid sample from said subject;

(2) quantitatively measuring the concentration of PGI in said sample from step (1);

(3) quantitatively measuring the concentration of G17 or stG17 in said sample from step (1);

(4) determining
a value for said Hp-marker by quantitatively measuring the enzyme immunoassay units (EIU) value of an *Helicobacter pylori* (Hp) antibody in said sample from step (1); and (5) entering into a data processing system comprising a data storing means or a display the PGI concentration, the G17 or stG17 concentration and the EIU value of the Hp antibody, wherein said data processing system comprises computer code which, when executed on a computer, performs the steps comprising:

(a) comparing said PGI concentration to a low PGI cut-off value (PGI-coI) of 20-30 µg/l and a high PGI cut-off value (PGI-coII) of 50 µg/l to obtain a PGI comparison result, (b) comparing said G17 concentration to a low G17 cut-off value (G17-coI) of 2.5 pmol/l and a high G17 cut-off value (G17-coII) of 5 pmol/l to obtain a G17 comparison result or comparing said stG17 concentration to a low stG17 cut-off value (stG17-coI) of 5 pmol/l and a high stG17 cut-off value (stG17-coII) of 10 pmol/l to obtain a stG17 comparison result, (c) comparing said Hp antibody value to an Hp antibody cut-off (Hp-co) value of 30 EIU to obtain an Hp antibody comparison result, and (d) combining the comparison results of steps 5(a), 5(b) and 5(c) to generate diagnosis information for the gastric mucosa of said subject according to the following table:

| PGI | G17 or stG17 | HP-Marker | Diagnosis |
|---|---|---|---|
| ≧20-30 µg/l | Any | ≦30 EIU | Normal |
| <20-30 µg/l | <10 pmol/l stG17 or <5 pmol/l G17 | ≦30 EIU | Atrophic antrum/ corpus gastritis |
| <20-30 µg/l | <5 pmol/l stG17 or <2.5 pmol/l G17 | >30 EIU | Atrophic antrum/ corpus gastritis | and stores or displays said diagnosis information, and
(6) using said stored or displayed diagnosis information to diagnose in said subject the condition of atrophic antrum/corpus gastritis.

17. A method for assessing the condition of the gastric mucosa in a subject to diagnose a condition of atrophic antrum gastritis by assaying pepsinogen I (PGI), unstimulated gastrin-17(G17) or stimulated gastrin-17 (stG17) and a marker for *Helicobacter pylori* infection (Hp-marker), the method comprising:
  (1) obtaining a serum, urine, saliva or lacrimal fluid sample from said subject;
  (2) quantitatively measuring the concentration of PGI in said sample from step (1);
  (3) quantitatively measuring the concentration of G17 or stG17 in said sample from step (1);
  (4) determining
    a value for said Hp-marker by quantitatively measuring the enzyme immunoassay units (EIU) value of an *Helicobacter pylori* (Hp) antibody in said sample from step (1); and
  (5) entering into a data processing system comprising a data storing means or a display the PGI concentration, the G17 or stG17 concentration and the EIU value of the Hp antibody, wherein said data processing system comprises computer code which, when executed on a computer, performs the steps comprising:
    (a) comparing said PGI concentration to a low PGI cut-off value (PGI-coI) of 20-30 µg/l and a high PGI cut-off value (PGI-coII) of 50 µg/l to obtain a PGI comparison result,
    (b) comparing said G17 concentration to a low G17 cut-off value (G17-coI) of 2.5 pmol/l and a high G17 cut-off value (G17-coII) of 5 pmol/l to obtain a G17 comparison result or comparing said stG17 concentration to a low stG17 cut-off value (stG17-coI) of 5 pmol/l and a high stG17 cut-off value (stG17-coII) of 10 pmol/l to obtain a stG17 comparison result,
    (c) comparing said Hp antibody value to an Hp antibody cut-off (Hp-co) value of 30 EIU to obtain an Hp antibody comparison result, and
    (d) combining the comparison results of steps 5(a), 5(b) and 5(c) to generate diagnosis information for the gastric mucosa of said subject according to the following table:

| PGI | G17 or stG17 | Antibody HP-Marker | Diagnosis |
|---|---|---|---|
| ≧20-30 µg/l | Any | ≦30 EIU | Normal |
| ≧20-30 µg/l | <5 pmol/l stG17 or <2.5 pmol/l G17 | >30 EIU | Atrophic antrum gastritis |
| <50 µg/l | 5-10 pmol/l stG17 or 2.5-5 pmol/l G17 | >30 EIU | Atrophic antrum gastritis | and stores or displays said diagnosis information, and
(6) using said stored or displayed diagnosis information to diagnose in said subject the condition of atrophic antrum gastritis.

18. A method for assessing the condition of the gastric mucosa in a subject to diagnose a condition of non-atrophic gastritis by assaying pepsinogen I (PGI), unstimulated gastrin-17(G17) or stimulated gastrin-17 (stG17) and a marker for *Helicobacter pylori* infection (Hp-marker), the method comprising:
  (1) obtaining a serum, urine, saliva or lacrimal fluid sample from said subject;
  (2) quantitatively measuring the concentration of PGI in said sample from step (1);
  (3) quantitatively measuring the concentration of G17 or stG17 in said sample from step (1);
  (4) determining
    a value for said Hp-marker by quantitatively measuring the enzyme immunoassay units (EIU) value of an *Helicobacter pylori* (Hp) antibody in said sample from step (1);
  and
  (5) entering into a data processing system comprising a data storing means or a display the PGI concentration, the G17 or stG17 concentration and the EIU value of the Hp antibody, wherein said data processing system comprises computer code which, when executed on a computer, performs the steps comprising:
    (a) comparing said PGI concentration to a low PGI cut-off value (PGI-coI) of 20-30 µg/l and a high PGI cut-off value (PGI-coII) of 50 µg/l to obtain a PGI comparison result,
    (b) comparing said G17 concentration to a low G17 cut-off value (G17-coI) of 2.5 pmol/l and a high G17 cut-off value (G17-coII) of 5 pmol/l to obtain a G17 comparison result or comparing said stG17 concentration to a low stG17 cut-off value (stG17-coI) of 5 pmol/l and a high stG17 cut-off value (stG17-coII) of 10 pmol/l to obtain a stG17 comparison result,
    (c) comparing said Hp antibody value to an Hp antibody cut-off (Hp-co) value of 30 EIU to obtain an Hp antibody comparison result,
  and
    (d) combining the comparison results of steps 5(a), 5(b) and 5(c) to generate diagnosis information for the gastric mucosa of said subject according to the following table:

| PGI | G17 or stG17 | HP-Marker | Diagnosis |
|---|---|---|---|
| ≧20-30 µg/l | Any | ≦30 EIU | Normal |
| ≧50 µg/l | 5-10 pmol/l stG17 or 2.5-5 pmol/l G17 | >30 EIU | Non-atrophic gastritis |
| ≧20-30 µg/l | >10 pmol/l stG17 or >5 pmol/l G17 | >30 EIU | Non-atrophic gastritis |
| ≧20-30 µg/l | >10 pmol/l stG17 or >5 pmol/l G17, | >30 EIU | Non-atrophic gastritis | and stores or displays said diagnosis information, and
(6) using said stored or displayed diagnosis information to diagnose in said subject the condition of non-atrophic gastritis.

19. A method for assessing the condition of the gastric mucosa in a subject to diagnose gastric mucosa conditions selected from the group consisting of atrophic corpus gastritis, atrophic antrum gastritis, atrophic antrum/corpus gastritis and non-atrophic gastritis by assaying (i) pepsinogen I (PGI), (ii) unstimulated gastrin-17 (G17) or stimulated gastrin 17 (stG17) and (iii) a marker for *Helicobacter pylori* infection (Hp-Marker), the method comprising:
   (1) obtaining a sample from said subject;
   (2) quantitatively measuring the concentration of PGI in said sample from step (1);
   (3) quantitatively measuring the concentration of G17 or stG17 in said sample from step (1);
   (4) determining
      a value for said Hp-marker by quantitatively measuring the enzyme immunoassay units (EIU) value of an *Helicobacter pylori* (Hp) antibody in said sample; and
   (5) entering into a data processing system comprising a data storing means or a display the PGI concentration, the G17 or stG17 concentration and the EIU value of the Hp antibody, wherein said data processing system comprises computer code which, when executed on a computer, performs the steps comprising:
      (a) comparing said PGI concentration to a low PGI cut-off value (PGI-coI) of 20-30 µg/l and a high PGI cut-off value (PGI-coII) of 50 µg/l to obtain a PGI comparison result,
      (b) comparing said G17 concentration to a low G17 cut-off value (G17-coI) of 2.5 pmol/l and a high G17 cut-off value (G17-coII) of 5 pmol/l to obtain a G17 comparison result or comparing said stG17 concentration to a low stG17 cut-off value (stG17-coI) of 5 pmol/l and a high stG17 cut-off value (stG17-coII) of 10 pmol/l to obtain a stG17 comparison result,
      (c) comparing said Hp antibody value to an Hp antibody cut-off (Hp-co) value of 30 EIU to obtain an antibody HP-marker comparison result, and
      (d) combining the comparison results of steps 5(a), 5(b) and 5(c) to generate diagnosis information for the gastric mucosa condition of said subject according to the following table:

| PGI | G17 or stG17 | HP-Marker | Diagnosis |
|---|---|---|---|
| ≧20-30 µg/l | Any | ≦30 EIU | Normal |
| <20-30 µg/l | ≧10 pmol/l stG17 or ≧5 pmol/l G17 | ≦30 EIU | Atrophic corpus gastritis |
| <20-30 µg/l | <10 pmol/l stG17 or <5 pmol/l G17 | ≦30 EIU | Atrophic antrum/corpus gastritis |
| <20-30 µg/l | <5 pmol/l stG17 or <2.5 pmol/l G17 | >30 EIU | Atrophic antrum/corpus gastritis |
| ≧20-30 µg/l | <5 pmol/l stG17 or <2.5 pmol/l G17 | >30 EIU | Atrophic antrum gastritis |
| <50 µg/l | 5-10 pmol/l stG17 or 2.5-5 pmol/l G17 | >30 EIU | Atrophic antrum gastritis |
| ≧50 µg/l | 5-10 pmol/l stG17 or 2.5-5 pmol/l G17 | >30 EIU | Non-atrophic gastritis |
| ≧20-30 µg/l | >10 pmol/l stG17 or >5 pmol/l G17 | >30 EIU | Non-atrophic gastritis |
| <20-30 µg/l | >10 pmol/l stG17 or >5 pmol/l G17 | >30 EIU | Atrophic corpus gastritis | and stores or displays said diagnostic information, and
(6) using said stored or displayed diagnosis information to diagnose in said subject a normal gastric mucosa condition or one or more gastric mucosa conditions selected from the group consisting of atrophic corpus gastritis, atrophic antrum/corpus gastritis, atrophic antrum gastritis and non-atrophic gastritis.

20. The method according to claim 19, further comprising:
   (a) quantitatively measuring the concentration of pepsinogen II (PGII) from said sample; and
   (b) forming a PGI/PGII ratio,
      wherein step(S) further comprises entering said PGI/PGII ratio into said data processing system, and wherein said data processing system further performs the step of:
      (5)(a') comparing said PGI/PGII ratio to a low PGI/PGII cut-off value (PGI/PGII-coI) of 2.5 µg/l and a high PGI/PGII cut-off value (PGI/PGII-co-II) of 5 µg/l to obtain a PGI/PGII combination comparison result, and wherein in step (5)(d) the comparison results of steps
      (5)(a), (5)(b) and (5)(c) are further combined with the comparison result of step (5)(a'), and wherein the diagnosis table is:

| PGI | PGI/PGII | G17 or stG17 | HP-Marker Antibody | Diagnosis |
|---|---|---|---|---|
| ≧20-30 µg/l | ≧2.5 | Any | ≦30 EIU | Normal |
| <20-30 µg/l | <2.5 | ≧10 pmol/l stG17 or ≧5 pmol/l G17 | ≦30 EIU | Atrophic corpus gastritis |
| <20-30 µg/l | <2.5 | <10 pmol/l stG17 or <5 pmol/l G17 | ≦30 EIU | Atrophic antrum/corpus gastritis |
| <20-30 µg/l | <2.5 | <5 pmol/l stG17 or <2.5 pmol/l G17 | >30 EIU | Atrophic antrum/corpus gastritis |
| ≧20-30 µg/l | ≧2.5 | <5 pmol/l stG17 or <2.5 pmol/l G17 | >30 EIU | Atrophic antrum gastritis |
| <50 µg/l | <5 | 5-10 pmol/l stG17 or 2.5-5 pmol/l G17 | >30 EIU | Atrophic antrum gastritis |
| ≧50 µg/l | ≧5 | 5-10 pmol/l stG17 or 2.5-5 pmol/l G17 | >30 EIU | Non-atrophic gastritis |

-continued

| PGI | PGI/PGII | G17 or stG17 | HP-Marker Antibody | Diagnosis |
|---|---|---|---|---|
| ≧20-30 µg/l | ≧2.5 | >10 pmol/l stG17 or >5 pmol/l G17 | >30 EIU | Non-atrophic gastritis |
| <20-30 µg/l | <2.5 | >10 pmol/l stG17 or >5 pmol/l G17. | >30 EIU | Atrophic corpus gastritis |

21. A method for assessing the condition of the gastric mucosa in a subject to diagnose a gastric mucosa condition of atrophic corpus gastritis by assaying pepsinogen I (PGI), unstimulated gastrin-17(G17) or stimulated gastrin-17 (stG17) and a marker for *Helicobacter pylori* infection (Hp-marker), the method comprising:

(1) obtaining a serum, urine, saliva or lacrimal fluid sample from said subject;
(2) obtaining a stool, breath or biopsy sample from said subject;
(3) quantitatively measuring the concentration of PGI in said sample from step (1);
(4) quantitatively measuring the concentration of G17 or stG17 in said sample from step (1);
(5) determining the presence or absence of an Hp antigen in a stool, breath or biopsy in said sample from step (2), and
(6) entering into a data processing system comprising a data storing means or a display the PGI concentration, the G17 or stG17 concentration and the presence or absence of the Hp antigen, wherein said data processing system comprises computer code which, when executed on a computer, performs the steps comprising:
  (a) comparing said PGI concentration to a low PGI cut-off value (PGI-coI) of 20-30 µg/l and a high PGI cut-off value (PGI-coII) of 50 µg/l to obtain a PGI comparison result,
  (b) comparing said G17 concentration to a low G17 cut-off value (G17-coI) of 2.5 pmol/l and a high G17 cut-off value (G17-coII) of 5 pmol/l to obtain a G17 comparison result or comparing said stG17 concentration to a low stG17 cut-off value (stG17-coI) of 5 pmol/l and a high stG17 cut-off value (stG17-coII) of 10 pmol/l to obtain a stG17 comparison result, and
  (c) combining the comparison results of steps 6(a), 6(b) and the presence or absence of the HP marker to generate diagnosis information for the gastric mucosa of said subject according to the following table:

| PGI | G17 or stG17 | HP-Marker | Diagnosis |
|---|---|---|---|
| ≧20-30 µg/l | Any | Absent | Normal |
| <20-30 µg/l | ≧10 pmol/l stG17 or ≧5 pmol/l G17 | Absent | Atrophic corpus gastritis |
| <20-30 µg/l | >10 pmol/l stG17 or >5 pmol/l G17 | Present | Atrophic corpus gastritis | and stores or displays said diagnosis information, and
(7) using said stored or displayed diagnosis information to diagnose in said subject the gastric mucosa condition of atrophic corpus gastritis.

22. A method for assessing the condition of the gastric mucosa in a subject to diagnose a condition of atrophic antrum/corpus gastritis by assaying pepsinogen I (PGI), unstimulated gastrin-17(G17) or stimulated gastrin-17 (stG17) and a marker for *Helicobacter pylori* infection (Hp-marker), the method comprising:

(1) obtaining a serum, urine, saliva or lacrimal fluid sample from said subject;
(2) obtaining a stool, breath or biopsy sample from said subject;
(3) quantitatively measuring the concentration of PGI in said sample from step (1);
(4) quantitatively measuring the concentration of G17 or stG17 in said sample from step (1);
(5) determining the presence or absence of an Hp antigen in said sample from step (2), and
(6) entering into a data processing system comprising a data storing means or a display the PGI concentration, the G17 or stG17 concentration and the presence or absence of the Hp antigen, wherein said data processing system comprises computer code which, when executed on a computer, performs the steps comprising:
  (a) comparing said PGI concentration to a low PGI cut-off value (PGI-coI) of 20-30 µg/l and a high PGI cut-off value (PGI-coII) of 50 µg/l to obtain a PGI comparison result,
  (b) comparing said G17 concentration to a low G17 cut-off value (G17-coI) of 2.5 pmol/l and a high G17 cut-off value (G17-coII) of 5 pmol/l to obtain a G17 comparison result or comparing said stG17 concentration to a low stG17 cut-off value (stG17-coI) of 5 pmol/l and a high stG17 cut-off value (stG17-coII) of 10 pmol/l to obtain a stG17 comparison result, and
  (c) combining the comparison results of steps 6(a), 6(b) and the presence or absence of the Hp antigen to generate diagnosis information for the gastric mucosa of said subject according to the following table:

| PGI | G17 or stG17 | HP-Marker | Diagnosis |
|---|---|---|---|
| ≧20-30 µg/l | Any | Absent | Normal |
| <20-30 µg/l | <10 pmol/l stG17 or <5 pmol/l G17 | Absent | Atrophic antrum/corpus gastritis |
| <20-30 µg/l | <5 pmol/l stG17 or <2.5 pmol/l G17 | Present | Atrophic antrum/corpus gastritis | and stores or displays said diagnosis information, and
(7) using said stored or displayed diagnosis information to diagnose in said subject the condition of atrophic antrum/corpus gastritis.

23. A method for assessing the condition of the gastric mucosa in a subject to diagnose a condition of atrophic antrum gastritis by assaying pepsinogen I (PGI), unstimulated gastrin-17(G17) or stimulated gastrin-17 (stG17) and a marker for *Helicobacter pylori* infection (Hp-marker), the method comprising:

(1) obtaining a serum, urine, saliva or lacrimal fluid sample from said subject;
(2) obtaining a stool, breath or biopsy sample from said subject;
(3) quantitatively measuring the concentration of PGI in said sample obtained from said subject in step (1);
(4) quantitatively measuring the concentration of G17 or stG17 in said sample obtained from said subject in step (1);
(5) determining the presence or absence of an Hp antigen in said sample from step (2), and
(6) entering into a data processing system comprising a data storing means or a display the PGI concentration, the G17 or stG17 concentration and either the EIU value of the Hp antibody or the Hp antigen status as Boolean parameter, wherein said data processing system comprises computer code which, when executed on a computer, performs the steps comprising:
 (a) comparing said PGI concentration to a low PGI cut-off value (PGI-coI) of 20-30 µg/l and a high PGI cut-off value (PGI-coII) of 50 µg/l to obtain a PGI comparison result,
 (b) comparing said G17 concentration to a low G17 cut-off value (G17-coI) of 2.5 pmol/l and a high G17 cut-off value (G17-coII) of 5 pmol/l to obtain a G17 comparison result or comparing said stG17 concentration to a low stG17 cut-off value (stG17-coI) of 5 pmol/l and a high stG17 cut-off value (stG17-coII) of 10 pmol/l to obtain a stG17 comparison result, and
 (c) combining the comparison results of steps 6(a), 6(b) and the presence or absence of said Hp antigen to generate diagnosis information for the gastric mucosa of said subject according to the following table:

| PGI | G17 or stG17 | HP-Marker | Diagnosis |
|---|---|---|---|
| ≧20-30 µg/l | Any | Absent | Normal |
| ≧20-30 µg/l | <5 pmol/l stG17 or <2.5 pmol/l G17 | Present | Atrophic antrum gastritis |
| <50 µg/l | 5-10 pmol/l stG17 or 2.5-5 pmol/l G17 | Present | Atrophic antrum gastritis | and stores or displays said diagnosis information, and
(7) using said stored or displayed diagnosis information to diagnose in said subject the condition of atrophic antrum gastritis.

24. A method for assessing the condition of the gastric mucosa in a subject to diagnose a condition of non-atrophic gastritis by assaying pepsinogen I (PGI), unstimulated gastrin-17(G17) or stimulated gastrin-17 (stG17) and a marker for *Helicobacter pylori* infection (Hp-marker), the method comprising:

(1) obtaining a serum, urine, saliva or lacrimal fluid sample from said subject;
(2) obtaining a stool, breath or biopsy sample from said subject;
(3) quantitatively measuring the concentration of PGI in said sample obtained from said subject in step (1);
(4) quantitatively measuring the concentration of G17 or stG17 in said sample obtained from said subject in step (1);
(5) determining the presence or absence of an Hp antigen in said sample from step (2); and
(6) entering into a data processing system comprising a data storing means or a display the PGI concentration, the G17 or stG17 concentration and the presence or absence of said Hp antigen, wherein said data processing system comprises computer code which, when executed on a computer, performs the steps comprising:
 (a) comparing said PGI concentration to a low PGI cut-off value (PGI-coI) of 20-30 µg/l and a high PGI cut-off value (PGI-coII) of 50 µg/l to obtain a PGI comparison result,
 (b) comparing said G17 concentration to a low G17 cut-off value (G17-coI) of 2.5 pmol/l and a high G17 cut-off value (G17-coII) of 5 pmol/l to obtain a G17 comparison result or comparing said stG17 concentration to a low stG17 cut-off value (stG17-coI) of 5 pmol/l and a high stG17 cut-off value (stG17-coII) of 10 pmol/l to obtain a stG17 comparison result, and
 (c) combining the comparison results of steps 6(a), 6(b) and the presence or absence of said Hp antigen to generate diagnosis information for the gastric mucosa of said subject according to the following table:

| PGI | G17 or stG17 | HP-Marker | Diagnosis |
|---|---|---|---|
| ≧20-30 µg/l | Any | Absent | Normal |
| ≧50 µg/l | 5-10 pmol/l stG17 or 2.5-5 pmol/l G17 | Present | Non-atrophic gastritis |
| ≧20-30 µg/l | >10 pmol/l stG17 or >5 pmol/l G17 | Present | Non-atrophic gastritis |
| ≧20-30 µg/l | >10 pmol/l stG17 or >5 pmol/l G17, | Present | Non-atrophic gastritis | and stores or displays said diagnosis information, and
(7) using said stored or displayed diagnosis information to diagnose in said subject the condition of non-atrophic gastritis.

25. A method for assessing the condition of the gastric mucosa in a subject to diagnose gastric mucosa conditions selected from the group consisting of atrophic corpus gastritis, atrophic antrum gastritis, atrophic antrum/corpus gastritis and non-atrophic gastritis by assaying (i) pepsinogen I (PGI), (ii) unstimulated gastrin-17 (G17) or stimulated gastrin 17 (stG17) and (iii) a marker for *Helicobater pylori* infection (Hp-Marker), the method comprising:

(1) obtaining a sample from said subject;
(2) quantitatively measuring the concentration of PGI in said sample obtained from said subject in step (1);
(3) quantitatively measuring the concentration of G17 or stG17 in said sample obtained from said subject in step (1);
(4) determining the presence or absence of an Hp antigen in said sample, and (5) entering into a data processing system comprising a data storing means or a display the PGI concentration, the G17 or stG17 concentration and either the EIU value of the Hp antibody or the presence or absence of said Hp antigen, wherein said data processing system comprises computer code which, when executed on a computer, performs the steps comprising:

(a) comparing said PGI concentration to a low PGI cut-off value (PGI-coI) of 20-30 µg/l and a high PGI cut-off value (PGI-coII) of 50 µg/l to obtain a PGI comparison result, (b) comparing said G17 concentration to a low G17 cut-off value (G17-coI) of 2.5 pmol/l and a high G17 cut-off value (G17-coII) of 5 pmol/l to obtain a G17 comparison result or comparing said stG17 concentration to a low stG17 cut-off value (stG17-co I) of 5 pmol/l and a high stG17 cut-off value (stG17-coII) of 10 pmol/l to obtain a stG17 comparison result ,and (c) combining the comparison results of steps 5(a), 5(b) and the presence or absence of said antigen Hp-marker to generate diagnosis information for the gastric mucosa condition of said subject according to the following table:

| PGI | G17 or stG17 | HP-Marker | Diagnosis |
|---|---|---|---|
| ≧20-30 µg/l | Any | Absent | Normal |
| <20-30 µg/l | ≧10 pmol/l stG17 or ≧5 pmol/l G17 | Absent | Atrophic corpus gastritis |
| <20-30 µg/l | <10 pmol/l stG17 or <5 pmol/l G17 | Absent | Atrophic antrum/corpus gastritis |
| <20-30 µg/l | <5 pmol/l stG17 or <2.5 pmol/l G17 | Present | Atrophic antrum/corpus gastritis |
| ≧20-30 µg/l | <5 pmol/l stG17 or <2.5 pmol/l G17 | Present | Atrophic antrum gastritis |
| <50 µg/l | 5-10 pmol/l stG17 or 2.5-5 pmol/l G17 | Present | Atrophic antrum gastritis |
| ≧50 µg/l | 5-10 pmol/l stG17 or 2.5-5 pmol/l G17 | Present | Non-atrophic gastritis |
| ≧20-30 µg/l | >10 pmol/l stG17 or >5 pmol/L G17 | Present | Non-atrophic gastritis |
| <20-30 µg/l | >10 pmol/l stG17 or >5 pmol/l G17 | Present | Atrophic corpus gastritis | and stores or displays said diagnostic information, and (6) using said stored or displayed diagnosis information to diagnose in said subject a normal gastric mucosa condition or one or more gastric mucosa conditions selected from the group consisting of atrophic corpus gastritis, atrophic antrum/corpus gastritis, atrophic antrum gastritis and non-atrophic gastritis.

26. The method according to claim 25, further comprising:

(a) quantitatively measuring the concentration of pepsinogen II (PGII) from said sample obtained from said subject in step (1); and (b) forming a PGI/PGII ratio, wherein step (5) further comprises entering said PGI/PGII ratio into said data processing system, and wherein said data processing system further performs the step of:

(5)(a') comparing said PGI/PGII ratio to a low PGI/PGII cut-off value (PGI/PGII-coI) of 2.5 µg/l and a high PGI/PGII cut-off value (PGI/PGII-co-II) of 5 µg/l to obtain a PGI/PGII combination comparison result, and wherein in step (5)(c) the comparison results of steps (5)(a), (5)(b) and the presence or absence of said HP marker are further combined with the comparison result of step (5)(a'), and wherein the diagnosis table is:

| PGI | PGI/PGII | G17 or stG17 | HP-Marker | Diagnosis |
|---|---|---|---|---|
| ≧20-30 µg/l | ≧2.5 | Any | Negative | Normal |
| <20-30 µg/l | <2.5 | ≧10 pmol/l stG17 or ≧5 pmol/l G17 | Negative | Atrophic corpus gastritis |
| <20-30 µg/l | <2.5 | <10 pmol/l stG17 or <5 pmol/l G17 | Negative | Atrophic antrum/corpus gastritis |
| <20-30 µg/l | <2.5 | <5 pmol/l stG17 or <2.5 pmol/l G17 | Positive | Atrophic antrum/corpus gastritis |
| ≧20-30 µg/l | ≧2.5 | <5 pmol/l stG17 or <2.5 pmol/l G17 | Positive | Atrophic antrum gastritis |
| <50 µg/l | <5 | 5-10 pmol/l stG17 or 2.5-5 pmol/l G17 | Positive | Atrophic antrum gastritis |
| ≧50 µg/l | ≧5 | 5-10 pmol/l stG17 or 2.5-5 pmol/l G17 | Positive | Non-atrophic gastritis |
| ≧20-30 µg/l | ≧2.5 | >10 pmol/l stG17 or >5 pmol/l G17 | Positive | Non-atrophic gastritis |
| <20-30 µg/l | <2.5 | >10 pmol/l stG17 or >5 pmol/l G17. | Positive | Atrophic corpus gastritis |

* * * * *